United States Patent
Kerwin et al.

[11] Patent Number: 5,957,894
[45] Date of Patent: Sep. 28, 1999

[54] INTRAVENOUS CONNECTION CLIP

[75] Inventors: Michael J. Kerwin; Alan B. Ranford, both of St. Louis; Daniel A. Talonn, University City, all of Mo.

[73] Assignee: Sherwood Services AG, Schaffhausen, Switzerland

[21] Appl. No.: 09/002,730

[22] Filed: Jan. 5, 1998

Related U.S. Application Data

[60] Provisional application No. 60/034,681, Jan. 3, 1997.

[51] Int. Cl.[6] ............................................. A61M 5/32
[52] U.S. Cl. ......................... 604/178; 604/905; 604/533; 285/88
[58] Field of Search ......................... 604/905, 178, 604/533, 538; 285/87, 88

[56] References Cited

U.S. PATENT DOCUMENTS

| | | |
|---|---|---|
| 805,579 | 11/1905 | Patchen . |
| 1,310,627 | 7/1919 | McEvilly . |
| 1,436,882 | 11/1922 | Knepper . |
| 2,691,201 | 10/1954 | Matthews . |
| 3,479,069 | 11/1969 | Sedam . |
| 3,609,638 | 9/1971 | Darrey . |
| 3,814,080 | 6/1974 | Norman ........................................ 61/17 |
| 3,881,753 | 5/1975 | Bochory ..................................... 285/92 |
| 3,937,499 | 2/1976 | Courtot ..................................... 285/319 |
| 4,224,937 | 9/1980 | Gordon ..................................... 128/133 |
| 4,230,109 | 10/1980 | Geiss ........................................ 128/214 |
| 4,270,778 | 6/1981 | Brownell ................................. 285/305 |
| 4,333,505 | 6/1982 | Jones et al. .............................. 141/383 |
| 4,405,312 | 9/1983 | Gross et al. .............................. 604/533 |
| 4,473,369 | 9/1984 | Lueders et al. ......................... 604/905 |
| 4,539,003 | 9/1985 | Tucker ..................................... 604/905 |
| 4,631,056 | 12/1986 | Dye ......................................... 604/111 |
| 4,704,177 | 11/1987 | Vaillancourt ............................ 156/226 |
| 4,792,163 | 12/1988 | Kulle ......................................... 285/88 |
| 4,826,486 | 5/1989 | Palsrok et al. .......................... 604/174 |
| 4,844,515 | 7/1989 | Field ....................................... 285/305 |
| 4,913,468 | 4/1990 | Rattmann ................................. 285/82 |
| 5,037,405 | 8/1991 | Crosby ................................... 604/533 |
| 5,192,273 | 3/1993 | Bierman et al. ........................ 604/905 |
| 5,209,529 | 5/1993 | Yan et al. ................................. 285/88 |
| 5,248,306 | 9/1993 | Clark et al. ............................. 604/283 |
| 5,360,237 | 11/1994 | Carman et al. ........................... 285/81 |
| 5,468,024 | 11/1995 | Carman et al. ........................... 285/81 |

*Primary Examiner*—Todd E. Manahan
*Attorney, Agent, or Firm*—David Warmbold; Douglas E. Denninger

[57] ABSTRACT

An intravenous connection clip for preventing separation of two tubular fluid flow connectors of respective intravenous (IV) tubing sets. The intravenous connection clip includes a generally tubular bracket for surrounding the fluid flow connectors and having large portions of the tube cut away to allow for easy visualization of the fluid flow connectors and the fluid path therethrough. The bracket of the IV connection clip having a generally "C" shaped port lock on a first end of the bracket having a pair of first arms for releasably gripping a conventional port of a first IV tubing set, a generally "U" shaped cannula and luer connector lock on an intermediate portion of the bracket for releasably contacting a conventional luer connector of a second IV tubing set fluidly coupled to the port of the first IV tubing set. The bracket further has a retaining clip on a second, or opposite, end of the bracket from the port lock having a pair of second arms for releasably gripping the tubing immediately adjacent the luer connector for assisting in preventing accidental disengagement of the fluid flow connectors. The second arms of the retaining clip further providing a strain relief or additional support for the tubing of the second tubing set, and retention of the IV connection clip on the tubing of the second tubing set away from the IV connectors for convenient storage between uses.

12 Claims, 4 Drawing Sheets

INTRAVENOUS CONNECTION CLIP

This application claims benefit of provisional application Ser. No. 60/034,681 filed Jan. 3, 1997.

FIELD OF THE INVENTION

The present invention relates to a clip device for a fluid connection system used to transfer fluids from one flow conduit to a second flow conduit. More particularly, the invention relates to an intravenous (IV) connection clip used to prevent the inadvertent or accidental disengagement of first and second tubing sets typically used in intravenous therapy.

BACKGROUND OF THE INVENTION

Intravenous therapy involves the flow of a therapeutic solution from a sterile container to a catheter or needle positioned in a patient's vein. One or more sterile tubing sets are required to transfer fluid from the container to the vein access device. Sterile connections with the tubing set can be made in a variety of ways. For example, connections can be made using conventional male and female luer connectors. Also, connections can be made using sharp needle connectors with resealable elastomeric septums. More recently, due to the concerns about accidental needle sticks, blunt cannula connectors have been utilized to connect an IV tubing set to a prepierced elastomeric septum for IV fluid tubing sets. Often times, the tubing sets have a number of "Y" sites provided having a prepierced elastomeric septum protruding off of the short "Y" side of the connector such that a blunt cannula connector can be introduced through the septum.

A primary concern with this type of tubing connector is the inadvertent or accidental disengagement of the tubing sets connection. An uninterrupted flow of solution or medicament to the patient is important to ensure proper medication and to prevent stasis in the flow, which could cause loss of the IV site on the patient due to thrombosis of the IV catheter.

The above concerns have led to medical guidelines and procedures that require that IV connections be secured together. A variety of securing mechanisms have been developed for securing IV connections. U.S. Pat. No. 4,224,937 discloses one such securing device having a cradle with an adhesive backing for adhesion to a patient's skin. The cradle is provided with a catheter hub retaining member for receiving the IV port, cannula and cannula hub after connection of the IV connection. The cradle includes a snap fit port connector to hold the whole assembly in place, and a lateral wall having a partial circular opening preventing relative axial movement between the port and cannula to prevent accidental disengagement of the IV connection once placed within the cradle.

U.S. Pat. No. 4,631,056 discloses a tamper discouraging system for use with an IV connection including a catheter with an elongated shaft and a hollow connector. The system includes first and second semi-annular shells for placement over the hollow connector. The first and second shells can be locked together to prevent dislodgment from the hollow connector. The system further includes a pair of arms and an arcuate flange connecting the arms at a distal end for contacting a shoulder of the elongated catheter to prevent axial disengagement of the catheter and connector when the system is in place thereabouts.

However, neither of the above securing devices are provided with features which grippingly lock onto both the port and cannula of a standard IV connection to prevent inadvertent disengagement of the cannula and port while also providing a retaining member for maintaining the security device about a tubing set when the securing device is not secured about the fluid flow connectors of the IV connection.

SUMMARY OF THE INVENTION

Therefore, it is a primary object of the invention to provide a simple and reliable IV connection clip for use in combination with IV fluid flow connectors.

It is another object of the invention to provide an IV connection clip that is easy to manipulate by medical personnel using the clip, yet reliable for securing the connectors of first and second intravenous tubing sets.

It is a further object of the invention to provide an IV connection clip that maximizes the visualization of the fluid path and IV fluid flow connectors without compromising the clip's reliability and security.

It is yet a further object of the invention to provide an IV connection clip that can be easily retained about one of the first and second tubing sets when the clip is otherwise not secured about the IV fluid connectors.

These and other objects of the invention are realized in the preferred embodiment of the IV connection clip for use in combination with typical fluid flow connectors, such as a port and cannula of first and second tubing sets, respectively. The IV connection clip comprises a generally cylindrical or tubular bracket for surrounding the fluid flow connectors having large portions of the tube cut away to allow for easy visualization of the fluid flow connectors and the fluid path therethrough. The bracket of the IV connection clip having a generally "C" shaped port lock on a first end of the bracket with a first pair of arms for releasably gripping a conventional port of a first IV tubing set, and a generally "U" shaped cannula and luer connector lock on an intermediate portion of the bracket for releasably contacting a conventional cannula and luer lock connector of a second IV tubing set fluidly coupled to the port of the first IV tubing set. The bracket further including a retaining clip on a second, or opposite, end of the bracket from the port lock having a pair of second arms for gripping the tubing immediately adjacent the luer connector for assisting in preventing accidental disengagement of the fluid flow connectors. The pair of second arms of the retaining clip further providing a strain relief or additional support for the tubing of the second tubing set.

Other features and advantages of the present invention will become readily apparent from the following detailed description, the accompanying drawings, and the appended claims.

DESCRIPTION OF THE PREFERRED EMBODIMENT

Figure 1:
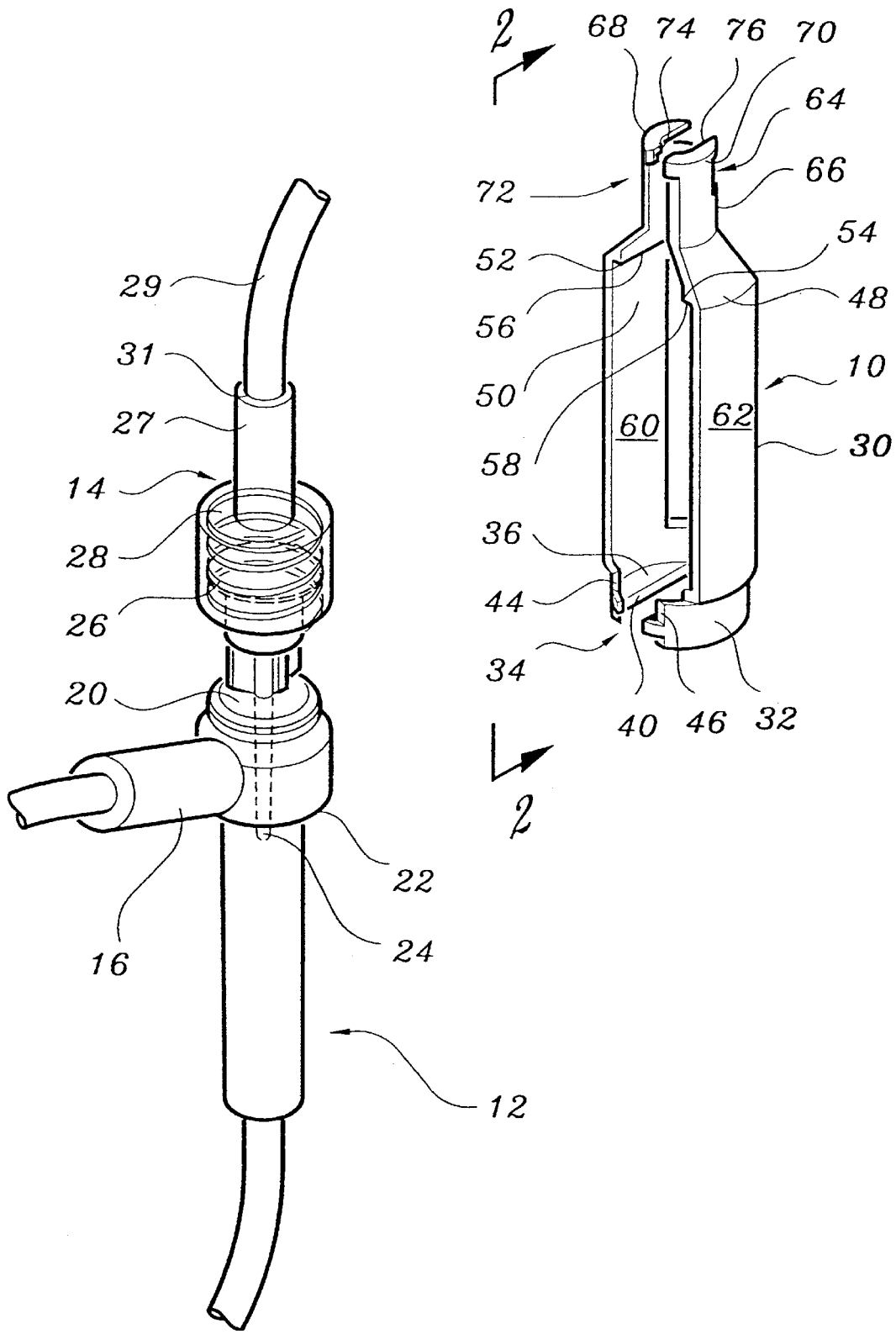
FIG. 1 is a perspective view of a typical first tubing set having a "Y" site connector and prepierced port with a blunt cannula of a second IV tubing set shown inserted into the port, and a perspective view of the IV connection clip of the present invention shown separated from the first and second tubing sets ready for connection therewith.

Referring to FIG. 1, an intravenous (IV) connection clip 10 is shown adjacent to a first IV tubing set 12 and a second IV tubing set 14. The first tubing set 12 typically provides fluid communication between a sterile fluid container (i.e. IV bottle, not shown) and a vein access device such as a catheter or needle (not shown) positioned into a patient's vein to assist medical personnel in stabilizing a patient's fluid intake, or otherwise to allow for the introduction of medicaments into a patient's blood stream. The first tubing set 12 may typically be provided with a "Y" site connector 16 having a port 18 with a prepierced elastomeric septum 20. The connector 16 further includes a first increased diameter radial shoulder 22 provided adjacent port 18. The second IV tubing set 14 may include, for example, a blunt cannula 24 secured to a standard luer connector 26 having an axially extending tubular portion 27 and an adjacent second increased diameter radial shoulder 28 between tubular portion 27 and cannula 24, the blunt cannula 24 being receivable through the prepierced septum 20 of port 18 to allow fluid communication from the second tubing set 14 to the first tubing set 12 and into the patient's vein access device. The tubular portion 27 connects axially to standard medical grade tubing 29. The tubular portion 27 of luer connector 26 has a diameter which is smaller than the second increased diameter radial shoulder 28 and greater than the diameter of tubing 29. A third increased diameter radial shoulder 31 is provided between tubular portion 27 and tubing 29.

However, it is not necessary that port 18 be specifically provided in a "Y" site connector as shown in the figures; it is only necessary that some kind of port be provided on a connector having an increased diameter radial shoulder adjacent the port. Furthermore, the cannula need not have a blunt tip or the port be prepierced; the cannula could be sharp and the port be provided with a septum which can be pierced.

Figure 2:
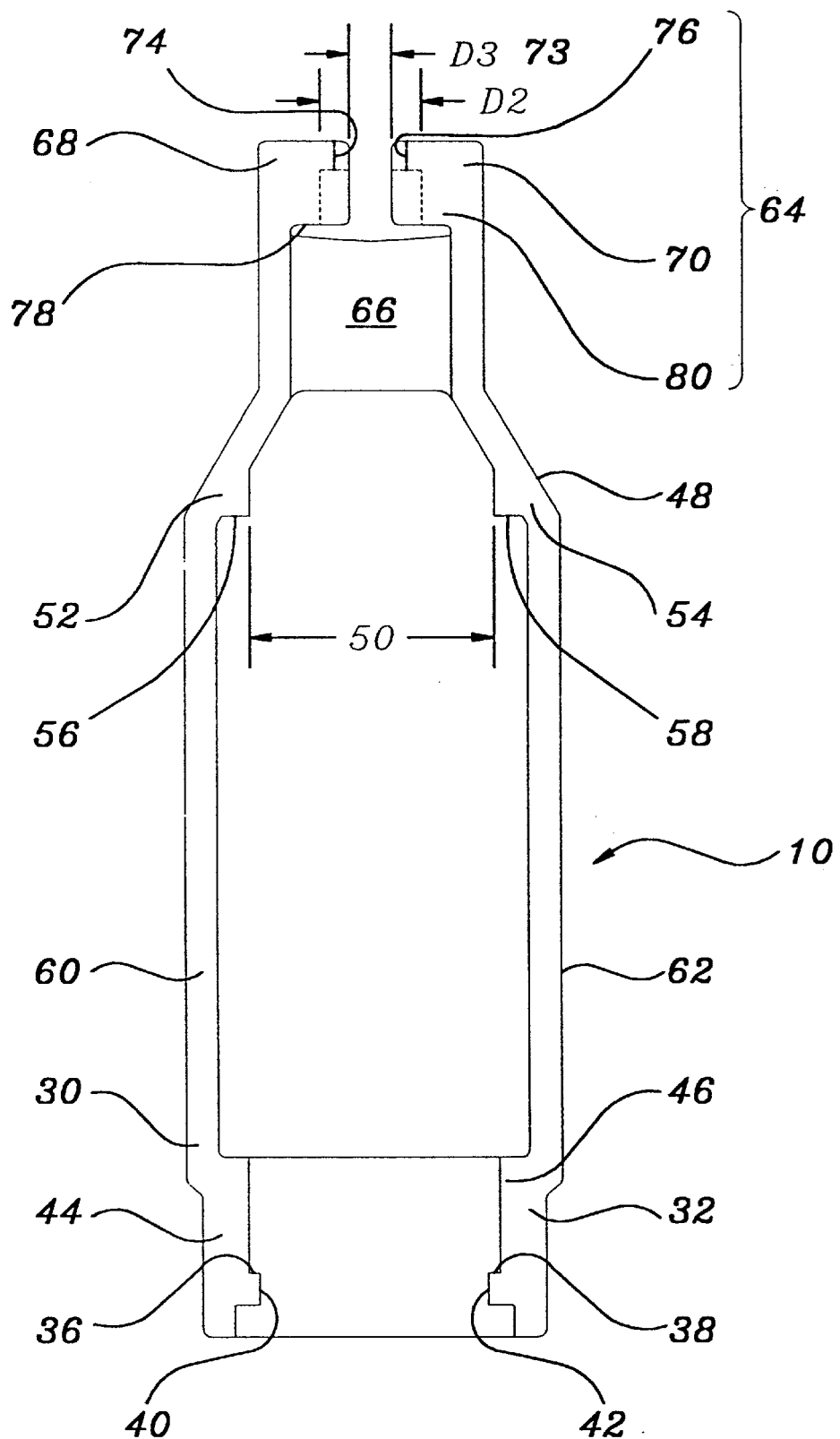
FIG. 2 is a side view of the IV connection clip taken along line 2—2 of FIG. 1.

The details of the IV connection clip 10 are best seen in FIGS. 1 and 2. The IV connection clip 10 includes a generally cylindrical or tubular bracket 30 for surrounding the port 18 and cannula 24/luer connector 26 to prevent axial disengagement of the port and cannula 24/luer connector 26. The tubular bracket has large areas cut away from the tube to allow for easy visualization of the fluid flow connectors 18 and 26 and the fluid path therethrough when in use. A generally "C" shaped port lock 32 is provided on the bottom end of bracket 30 as shown in FIG. 1 having a pair of first arms 44 and 46 with a first opening 34 provided between said first arms 44 and 46 of the "C" shape port lock 32. The port lock 32 further includes a pair of first shoulders 36 and 38 extending radially inwards towards the longitudinal axis of bracket 30, the first shoulders 36 and 38 having parallel guiding surfaces 40 and 42, respectively, for assisting in properly positioning the port lock 32 about port 18. The first shoulders 36 and 38 are adapted to abut against the first increased diameter radial shoulder 22 of port 18 of first IV tubing set 12 when IV connection clip 10 is installed in place about the fluid flow connectors. The distance between first arms 44 and 46 of port lock 32 is less than the diameter of the port 18 at the point immediately adjacent and above the first increased diameter radial shoulder 22 as seen in FIG. 1 to allow the port lock 32 to have a snap fit about port 18.

The bracket 30 further including a generally "U" shaped cannula and luer connector lock 48 positioned at an intermediate portion of the bracket 30 having an opening 50 between ends 52 and 54 of the "U" shaped cannula and luer connector lock 48. The cannula and luer connector lock 48 further includes a pair of second shoulders 56 and 58 extending radially inwardly toward the axial axis of bracket 30. The second shoulders 56 and 58 are adapted to abut against the second increased diameter radial shoulder 28 of luer connector 26 of the second IV tubing set 14 when the IV connection clip is installed in place about the fluid flow connectors. The cannula and luer connector lock 48 being connected to port lock 32 by a pair of partially arcuate side members 60 and 62 which provide for stabilization and strength against axial pull and transverse pushing forces.

The bracket 30 further including a retaining clip 64 on its second, or opposite, end of the bracket 30 from port lock 32. The retaining clip 64 having a partial tubular axial wall 66 extending upwardly from the cannula and luer connector lock 48 as seen in FIG. 1. The axial wall 66 having a pair of second arms 68 and 70 extending axially and radially to provide a second flexible opening 72 between the pair of second arms 68 and 70. Each second arm 68 and 70 further having parallel second guiding surfaces 74 and 76 facing each other, the distance D2 between second guiding surfaces 74 and 76 being very slightly smaller than the diameter of tubing 29. The distance D2 between the second guiding surfaces 74 and 76 is important so as to allow the IV connection clip to be slid up the tubing 29 and for holding the clip in the same position on tubing 29 when not in use and as further described below. Retaining clip shoulders 78 and 80 are provided adjacent second guiding surfaces 74 and 76, respectively, facing the first end of bracket 30. The distal most portion of the second arms 68 and 70 extending towards one another such that the distance D3 between the second arms 68 and 70 is substantially shorter than the diameter of tubing 29 to allow the retaining clip 64 to have a snap fit about tubing 29 of the second IV tubing set 14 when the IV connection clip is installed in place about the fluid flow connectors. The distance D3 is visibly shorter than the distance D2 so that once the IV connection clip is in place about tubing 29 it can only be removed from about the tubing 29 by intentional action by the medical personnel utilizing the IV tubing sets.

The IV connection clip 10 is preferably molded of a suitable flexible plastic such as polypropylene. However, other plastic materials such as polyvinyl chloride, polystyrene or other medical grade flexible material are suitable. The IV connection clip could also be made out of a metal material with appropriate design modifications.

To further ensure that the IV connection clip is not unintentionally removed from the IV connectors, an additional strap (not shown) may be included which would close the opening 34 between first arms 44 and 46 of the "C" shaped port lock 32. The strap could be molded as part of the IV connection clip 10 or could be a separate component.

Figure 3:
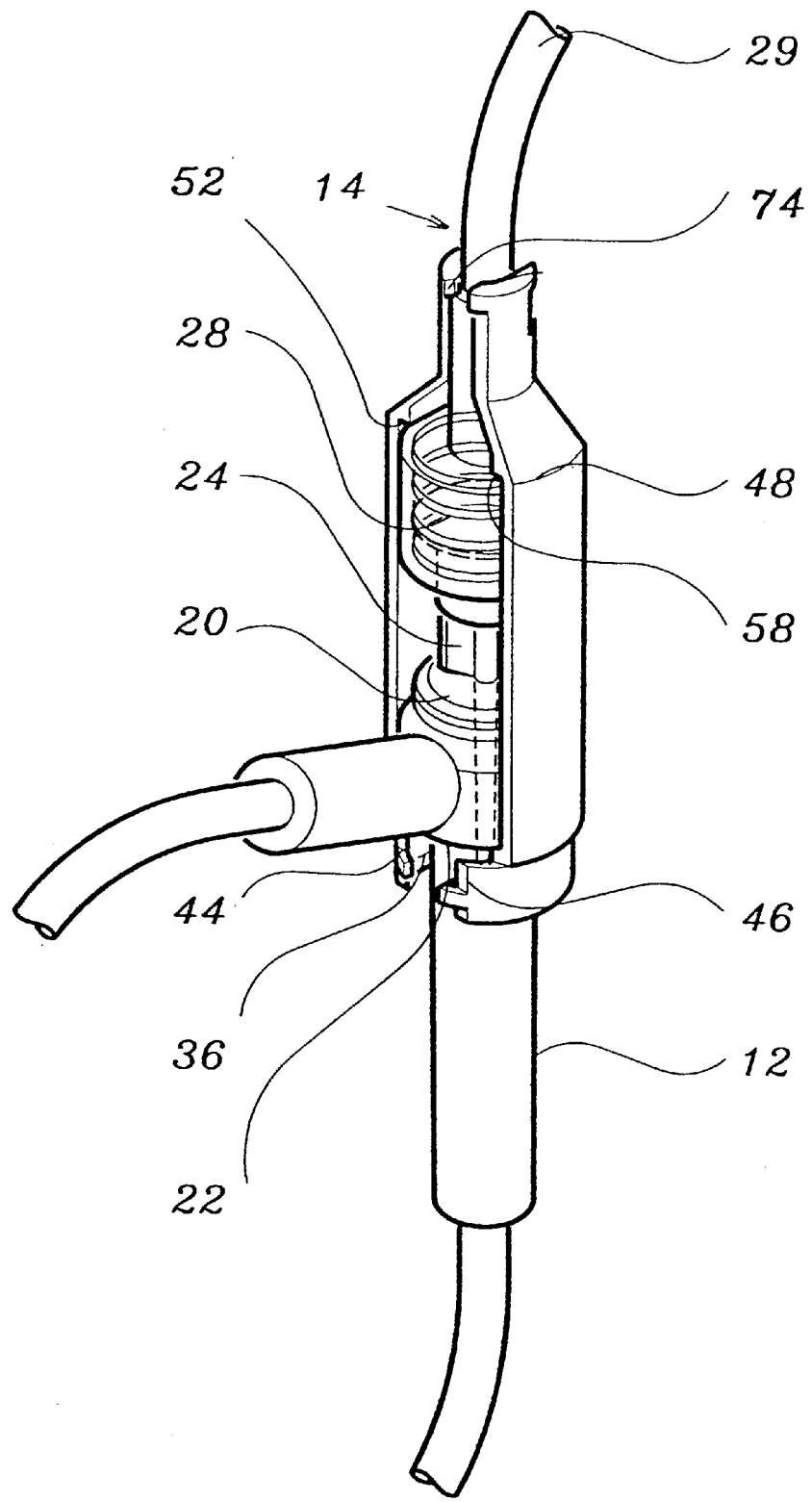
FIG. 3 is a perspective view of the first and second IV tubing sets of FIG. 1 with the IV connection clip of the present invention shown clipped in place about the fluid flow connectors of the first and second tubing sets to prevent axial disengagement thereof.
Figure 4:
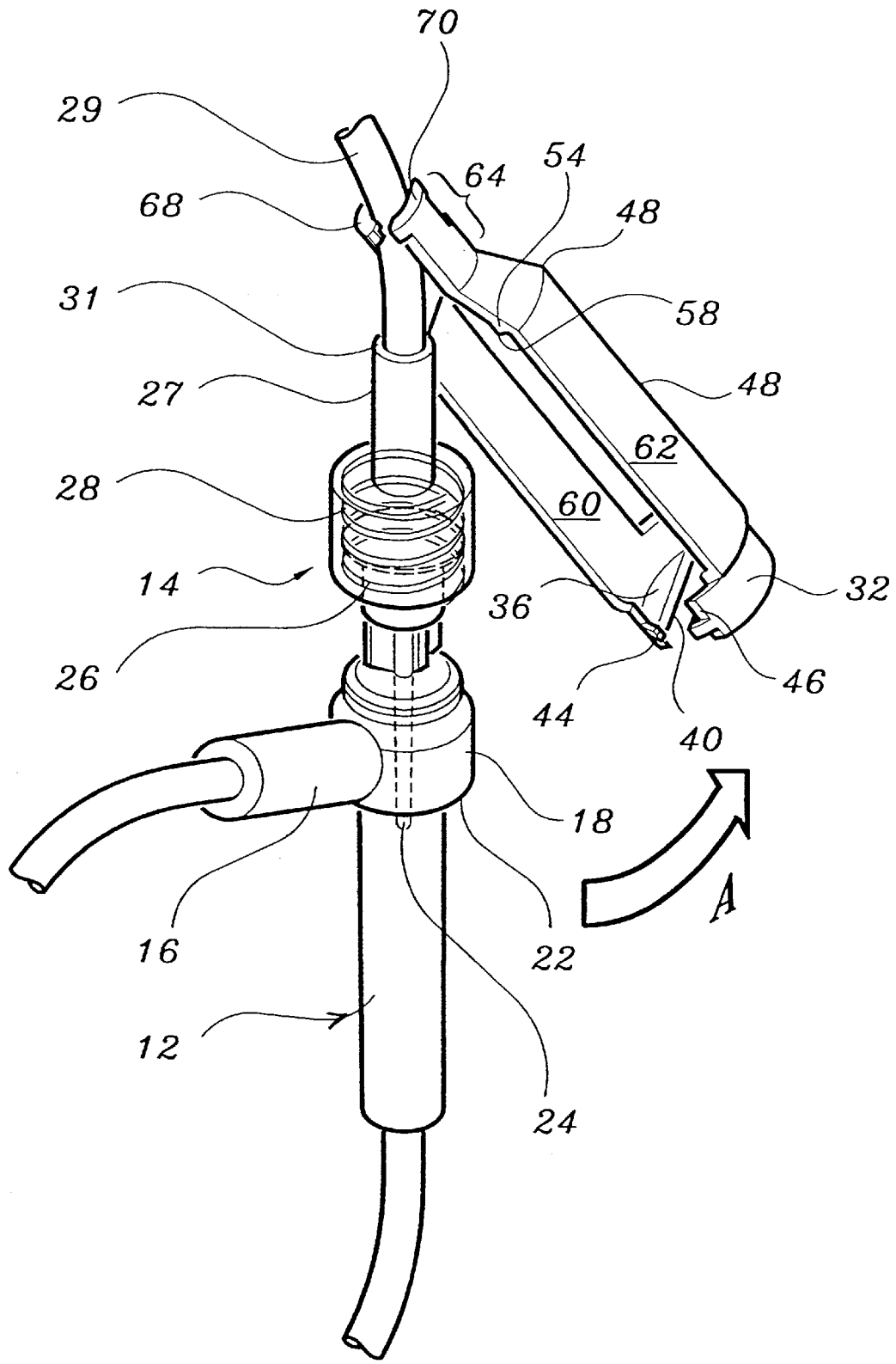
FIG. 4 is a perspective view of the first and second IV tubing sets of FIG. 1 shown with the IV connection clip being retained about the tubing of the second IV tubing set and otherwise not secured about the fluid flow connectors of the first and second IV tubing sets.

Referring now to FIGS. 3 and 4, the method of attachment of the IV connection clip 10 to the fluid flow connectors of the first and second IV tubing sets 12 and 14, respectively, to prevent axial disengagement thereof is shown in greater detail. As best seen in FIG. 1, the first IV tubing set 12 is shown with the blunt cannula 24 of the second IV tubing set 14 piercing the prepierced septum 20 of port 18. Referring now to FIGS. 3 and 4, the IV connection clip 10 is shown clipped or attached in place about the fluid flow connectors of the first and second IV tubing sets 12 and 14, respectively. The first shoulders 36 and 38 of port lock 32 are shown abutting the first increased diameter radial shoulder 22 of port 18 with first arms 44 and 46 clipped around port 18. The second shoulders 56 and 58 of the cannula and luer connector lock 48 are abutting the second increased diameter radial shoulder 28 of luer connector 26 and retaining clip shoulders 78 and 80 are abutting the third increased diameter radial shoulder 31 of luer connector 26 with second flexible arms 68 and 70 of retaining clip 64 clipped around tubing 29. The IV connection clip 10 of the present invention will prevent axial disengagement of the cannula 24 from the port 18. Axial disengagement or relative movement between cannula 24 and port 18, in some cases, is prevented due to the contact between the first and second increased diameter radial shoulders 22 and 28 of port 18 and luer connector 26, respectively, with the first shoulders 36 and 38 and second shoulders 56 and 58. In other cases, axial disengagement of the cannula 24 from the port 18 is prevented due to contact between the increased diameter radial shoulders 22 and 31 of port 18 and luer connector 26, respectively, with the first shoulders 36, 38 and second shoulders 78 and 80 of the port lock 32 and the retaining clip 64, respectively.

Additionally, the first arms 44 and 46 of the port lock 32 and second arms 68 and 70 of retaining clip 64 will act to prevent the IV connection clip 10 from being accidentally or easily bumped off of the fluid flow connectors of the first and second IV tubing sets 12 and 14 by medical personnel on the patient.

It may be necessary for medical personnel to expose port 18 for the purpose of alcohol prepping and insertion of a fresh cannula into the port 18. Referring to FIG. 4, the IV connection clip 10 is shown tilted out of the way of the fluid flow connectors, while yet still being retained about tubing 29 of the second IV tubing set 14. This is accomplished by unclipping the port lock first arms 44 and 46 from about port 18 and moving the IV connection clip 10 in the direction of arrow A as shown in FIG. 4 and pushing the IV connection clip 10 up the tubing 29 of the second IV tubing set with the retaining clip second arms 68 and 70 still clipped about tubing 29. In this fashion the IV connection clip 10 can be removed from about the port 18, cannula 24, and luer connector 26 and tilted out of the way to expose port 18 for alcohol prepping or to simply retain the IV connection clip on the second IV tubing set between uses. Since the distance D2 between second guiding surfaces 74 and 76 is slightly smaller than the diameter of tubing 29, the IV connection clip can be easily slid up or down on the tubing 29 and the clip will tend to stay in the position where it is left by the medical personnel using the IV connection clip. Additionally, the IV connection clip will not readily slip back down the tubing 29 once the clip up on the tubing 29 in a position which is out of the way of the IV connectors.

It is also possible that the retaining clip can be located adjacent the port lock such that the IV connection clip could be retained about the first IV tubing set instead of the second IV tubing set when not in use.

It is to be understood, however, that since changes may be made in the above described clip device, especially in matters of shape, size, and/or material used, without departing from the scope of the invention herein described, it is intended that all matter contained in the above description or shown in the accompanying drawings shall be interpreted in an illustrative and not in a limiting sense. For example, it is not entirely necessary that the first and second openings be flexible. Such openings could be slip-fitted about the cannula and luer connector, and port connector, respectively. The present invention is indicated by the broad general meaning of the terms in which the appended claims are expressed.

We claim:

1. An intravenous connection clip for preventing separation and fluid leakage between a port of a first intravenous tubing set axially connected in fluid flow communication with a cannula and luer connector of a second intravenous tubing set, the port having a first increased diameter radial shoulder, the luer connector having an axially extending tubular portion with a second increased diameter radial shoulder adjacent and coaxial to the cannula on a first end, the tubular portion being coaxially connected on its second end to tubing having a smaller diameter than the diameter of the tubular portion to provide a third increased diameter radial shoulder therebetween, the intravenous connection clip comprising:

a generally tubular bracket having a first end, an intermediate portion, and a second end;

a port lock provided at said first end having a pair of first arms and a first flexible opening between said first arms, and a pair of first shoulders facing the second end so as to be radially attachable to the port of the first intravenous tubing set adjacent to the first increased diameter radial shoulder;

a cannula and luer connector lock provided at the intermediate portion of said bracket having a pair of second shoulders facing the first end of the bracket so as to be radially attachable to the luer connector of the second intravenous tubing set adjacent to the second increased diameter radial shoulder; and a retaining clip provided at the second end of the bracket having a pair of second arms and a second flexible opening between said second arms so as to be radially attachable to the tubing of the second intravenous tubing set adjacent to the third increased diameter radial shoulder.

2. The intravenous connection clip of claim 1, wherein the retaining clip further includes a pair of third shoulders facing the first end of the bracket, the first, second, and third shoulders of the port lock, cannula and luer connector lock, and retaining clip, respectively, abut the first, second, and third increased diameter radial shoulders of the port, and first and second ends of the luer connector, respectively.

3. The intravenous connection clip of claim 1, wherein the first and second flexible openings of the port lock and retaining clip, respectively, are dimensioned so as to attach to the port of the first intravenous tubing set and tubing adjacent the luer connector of the second intravenous tubing set with a snap fit.

4. The intravenous connection clip of claim 1, wherein the bracket can be removed from about the port of the first intravenous tubing set and luer connector of the second intravenous tubing set while still being retained about the tubing of the second intravenous tubing set so as to allow the cannula to be removed from the port to separate the first and second intravenous tubing sets.

5. The intravenous connection clip of claim 1, wherein the retaining clip provided at the second end of the bracket has a reduced internal diameter so as to provide additional support and stiffness to the tubular portion of the luer connector.

6. The intravenous connection clip of claim 5, wherein the second arms of the retaining clip are provided with surfaces facing each other spaced apart a distance very slightly smaller than the outside diameter of the tubing of the second intravenous tubing set to provide additional support and stiffness to said tubing and to provide a friction between said surfaces and said tubing to allow the intravenous connection clip to be retained about the tubing in any particular position once left there while still being allowed to be intentionally slid up or down on the tubing relative to the cannula and luer connector of the second intravenous tubing set.

7. The intravenous connection clip of claim 6, wherein the retaining clip surfaces are parallel.

8. The intravenous connection clip of claim 1, wherein the port lock is provided with a pair of guiding surfaces facing each other spaced apart a distance slightly greater than the diameter of the port immediately below the first increased diameter radial shoulder for assisting on guiding the port lock into position about the port of the first intravenous tubing set.

9. The intravenous connection clip of claim 8, wherein the port guiding surfaces are parallel.

10. The intravenous connection clip of claim 1, wherein the generally tubular bracket is cut out on two opposing sides between the port lock at the first end of said bracket to the retaining clip at the second end of said bracket to maximize visualization of the port, and luer connector of the first and second intravenous tubing sets and the fluid flow path therethrough.

11. The intravenous connection clip of claim 10, wherein the port lock and cannula and luer connector lock are connected by an arcuate side member extending axially to the longitudinal axis of the tubular bracket.

12. The intravenous connection clip of claim 11, wherein the port lock and cannula and luer connector lock are connected by a pair of generally arcuate side members extending axially to the longitudinal axis of the tubular bracket.

* * * * *